(12) United States Patent
Rabbeth, Jr.

(10) Patent No.: US 10,905,181 B2
(45) Date of Patent: Feb. 2, 2021

(54) GLOVE PREVENTING HYPER-EXTENDED OR JAMMED FINGERS

(71) Applicant: Robert Sydney Rabbeth, Jr., Simi Valley, CA (US)

(72) Inventor: Robert Sydney Rabbeth, Jr., Simi Valley, CA (US)

(*) Notice: Subject to any disclaimer, the term of this patent is extended or adjusted under 35 U.S.C. 154(b) by 645 days.

(21) Appl. No.: 14/744,626

(22) Filed: Jun. 19, 2015

(65) Prior Publication Data
US 2015/0366277 A1 Dec. 24, 2015

Related U.S. Application Data

(63) Continuation of application No. 62/014,459, filed on Jun. 19, 2014.

(51) Int. Cl.
| | |
|---|---|
| *A41D 19/015* | (2006.01) |
| *A63B 71/14* | (2006.01) |
| *A61F 5/01* | (2006.01) |
| *A41D 13/08* | (2006.01) |

(52) U.S. Cl.
CPC ........ *A41D 19/01588* (2013.01); *A61F 5/013* (2013.01); *A63B 71/141* (2013.01); *A41D 13/087* (2013.01)

(58) Field of Classification Search
CPC ........ A41D 19/01517; A41D 19/01582; A41D 19/1523; A41D 19/01588; A41D 13/08; A41D 13/081; A41D 13/0821; A41D 13/084; A61F 5/0111; A61F 5/0118; A61F 5/05866

USPC .......... 2/16, 20, 21, 161.1, 161.6, 161, 455; 128/878–880; 602/20–22
See application file for complete search history.

(56) References Cited

U.S. PATENT DOCUMENTS

| | | | | |
|---|---|---|---|---|
| 4,272,849 | A * | 6/1981 | Thurston | A41D 19/01517 2/16 |
| 5,117,509 | A * | 6/1992 | Bowers | A41D 19/01547 2/161.1 |
| 6,044,494 | A * | 4/2000 | Kang | A41D 19/01547 2/161.1 |
| 6,065,155 | A * | 5/2000 | Sandusky | A63B 71/148 2/161.1 |
| 6,342,043 | B1 | 1/2002 | Gottsmann | |
| 6,557,177 | B2 | 5/2003 | Hochmuth | |
| 6,725,466 | B2 | 4/2004 | Hochmuth | |
| 6,918,137 | B2 | 7/2005 | Fowler | |
| 7,143,447 | B2 | 12/2006 | Fleischmann | |

(Continued)

*Primary Examiner* — Gloria M Hale

(57) ABSTRACT

A glove used in sports such as football, soccer, basketball, volleyball, snowboarding or motorcycle riding or work such as construction or heavy machinery operation that includes stiffening components attached on top of each finger portion of the glove and anchored beyond the base knuckle on top of the glove to prevent the fingers from hyper-extending or jamming and creating a protective exoskeleton for the entire hand while minimally affecting the degree of freedom and range of motion for the fingers. Each stiffening component is comprised of multiple slits or hinges as well as a sliding swivel pivot hinge which allow the stiffening components to bend in unison with each finger but lock in place to form a solid element and prevent the fingers from hyper-extending when the finger and its accompanying stiffening component are straightened.

11 Claims, 2 Drawing Sheets

(56) References Cited

U.S. PATENT DOCUMENTS

| | | | |
|---|---|---|---|
| 7,293,296 B1 | 11/2007 | Beraznik | |
| 7,320,145 B2 | 1/2008 | Hochmuth | |
| 7,406,720 B2 | 8/2008 | Hoelscher | |
| 7,574,748 B2 | 8/2009 | Fisher et al. | |
| 7,607,178 B2 | 10/2009 | DeBlasis | |
| 7,797,758 B2 | 9/2010 | Keppler | |
| 7,862,524 B2 | 1/2011 | Carignan | |
| 7,958,568 B2 | 6/2011 | Fisher et al. | |
| 8,029,414 B2 | 10/2011 | Ingvast et al. | |
| 8,037,549 B2 * | 10/2011 | Saur | A41D 19/01582 2/455 |
| 8,262,594 B2 * | 9/2012 | Sandusky | A61F 5/0111 128/878 |
| 8,341,763 B2 | 1/2013 | Geyer et al. | |
| 8,490,215 B2 | 7/2013 | Mueller | |
| 8,646,112 B2 | 2/2014 | Nix | |
| 8,678,980 B2 | 3/2014 | Land | |
| 8,849,453 B2 | 9/2014 | Bergelin et al. | |
| 2005/0114982 A1 | 6/2005 | Gremmert | |
| 2007/0028354 A1 * | 2/2007 | Hochmuth | A41D 19/01523 2/161.1 |
| 2008/0009771 A1 | 1/2008 | Perry | |
| 2009/0162651 A1 * | 6/2009 | Rios | A43B 13/04 428/354 |
| 2009/0307821 A1 * | 12/2009 | Chang | A41D 19/01588 2/21 |
| 2010/0325777 A1 * | 12/2010 | Radhakrishnan | A41D 19/01558 2/161.1 |

* cited by examiner

GLOVE PREVENTING HYPER-EXTENDED OR JAMMED FINGERS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM, LISTING COMPACT DISC APPENDIX

Not Applicable

BACKGROUND OF THE INVENTION

1. Field of the Invention

The present invention relates to an article of clothing, in particular a glove, that can be used in work or sport, which prevents the fingers from hyper-extending or jamming and acts as an exoskeleton protecting the hand.

2. Description of Related Art

There are many gloves containing stiffening components to prevent the fingers from hyper-extending or jamming which can be used while working or participating in sports. Numerous patents have been filed referencing stiffening components that are attached to a glove in order to prevent the user's fingers from hyper-extending or jamming. However, in all of these patents the stiffening components are attached to the glove from the tip of the glove's finger to beyond the base knuckle in one solid connection. This solid connection inhibits the glove wearer's fingers from moving in their natural positions. Therefore, there is a substantial need for a glove with stiffening components that are affixed in such a way as to allow full finger movement.

There are many gloves containing stiffening components to prevent the fingers from hyper-extending or jamming which can be used while working or participating in sports but they share a common flaw. These designs do curtail hyper-extension injuries but they drastically inhibit the mobility of the wearer's fingers because the stiffening component is pressing on top of the finger for the full length of the digit, limiting mobility. Examples of this can be found in U.S. Pat. No. 8,037,549 to Saur and Knappworst for a Reinforcing Element, U.S. Pat. No. 8,490,215 to Mueller and Meythaler for a Reinforcing Element, U.S. Pat. No. 8,341,763 to Geyer et al. for a Reinforcing Element and U.S. Pat. No. 8,646,112 to Nix and Schwartz for a Reinforcing Element For A Glove in which the stiffening components are referred to as "reinforcing elements." In U.S. Pat. No. 6,557,177 B2 to Hochmuth for a Glove With A Reinforcement Strip and U.S. Pat. No. 6,725,466 B2, also to Hochmuth for a Reinforcing Strip For A Goalkeeper's Glove, the stiffening component is referred to as a "reinforcement strip." In U.S. Pat. No. 7,574,748 to Fisher et al. for a Glove With Support System and U.S. Pat. No. 7,958,568, also to Fisher et al. for a Glove With Support System, the stiffening components are referred to as "support systems." In U.S. Pat. No. 7,293,296 to Beraznik and Makela for a Football Glove And Method Of Use the stiffening components are referred to as "unidirectional stiffeners." In U.S. Pat. No. 7,607,178 to DeBlasis for a Goalkeeper's Glove With Protective Fingertip Extension the stiffening components are referred to as "extensions with attachment legs" and in U.S. Pat. No. 7,143,447 B2 to Fleischmann for a Finger Protector the stiffening components are referred to as "finger protectors." None of these designs allow the fingers to move in their natural positions because none have the equivalent of a sliding swivel pivot hinge which means all of the stiffening components in the previously mentioned prior art sit directly on top of the finger portions of the gloves with no space between the stiffening component and the glove, inhibiting mobility. There is a need for a glove which prevents hyper-extension but allows full finger mobility and the present invention satisfies that need with the sliding swivel pivot hinge.

Some prior art does reference designs which are similar to the present invention's sliding swivel pivot hinge but these designs are used for shoulder harnesses. U.S. Pat. No. 6,342,043 to Gottsmann for a Swivelling Fracture Othosis includes a "joint shaft" that "engages in a swivellable manner." This "joint shaft" allows the wearer to loosen or tighten the othosis without removing the entire apparatus and serves a different function than the present invention's sliding swivel pivot hinge. The present invention's sliding swivel pivot hinge acts as a base which allows the finger to move freely and also stops the stiffening component once it reaches a certain point, preventing the finger from hyper-extending. The "joint shaft" does allow additional movement but does not prohibit the shoulder from moving past a certain point like the present invention's sliding swivel pivot hinge. U.S. Pat. No. 7,862,524 B2 to Carignan and Liszka for a Portable Arm Exoskeleton For Shoulder Rehabilitation includes a series of "links" and "axis" to create "rotational joints" but these rotational joints are designed to limit the degree of freedom for the arm and the present invention's sliding swivel pivot hinge is designed to increase the degree of freedom for the fingers. US 20080009771 A1 to Perry and Rosen for an Exoskeleton also incorporates a series of "axis" to form "joints" in a shoulder harness but like U.S. Pat. No. 7,862,524 B2, this design limits degree of freedom for an arm while the present invention's design increases the degree of freedom for the fingers.

The prior art showing designs similar to the present invention's sliding swivel pivot hinge is not limited to shoulder harnesses. There is also prior art for gloves that incorporate some but not all of the features of the sliding swivel pivot hinge. U.S. Pat. No. 7,797,758 to Keppler and Spitzer for a Glove Reinforcement has a design that includes a "plate" in which "nipples" are pushed through holes so that the mobility of the members (fingers) is impeded in only one direction. The present invention's design is different in that the bottom of each protruding base in the sliding swivel pivot hinges could be considered a plate but there is a separate plate for each individual stiffening component and U.S. Pat. No. 7,797,758 uses one big plate for all five stiffening components protecting the fingers. One big plate resting on top of the hand inhibits movement of the hand while five separate plates allow freer movement of the hand. Also, U.S. Pat. No. 7,797,758 uses holes while the present invention uses slots. Holes limit movement of the fingers while slots allow movement and in order for the nipples to fit into the holes they have to be made of flexible material. This flexible material does enable the nipples to fit into the accompanying holes but when the fingers on the glove are pushed back in a manner that causes hyper-extension the flexible nipple will continue to bend and will not prevent the stiffening components attached to the fingers from stopping. U.S. Pat. No. US 20090307821 A1 to Chang for a Hand Protection Structure also includes holes for receiving the back of a stiffening component, referred to as a "finger protection unit," but they are mounted directly onto the back of the hand in a hole and that limits the degree of freedom for the fingers. The slot in the present invention's design allows the stiffening component to move forward and back as well as side to side where the hole in the design for U.S. Pat. No. US 20090307821 only allows for side to side movement. Plus, the entire stiffening component for U.S. Pat. No. US 20090307821 sits directly on top of the finger portion of the glove for the full length of the finger and the stiffening component in the present invention's design is only attached to the front end of the finger portion of the glove and beyond the base knuckle on the dorsal side of the glove, leaving a gap between the majority of the stiffening component and the glove, allowing additional degree of freedom for the fingers. U.S. Pat. No. 7,320,145 to Hochmuth for a Glove Reinforcement has a design that includes a "stopping shank, stopping hub, stopping fastener and corridor." This design is used to secure the elements which make up the stiffening components and in no way resembles or functions in a manner similar to the present invention's sliding swivel pivot hinge which provides an anchor and stopping point. The stiffening components in U.S. Pat. No. 7,320,145 are referred to as "reinforcements" and like all of the other designs, excluding the present invention's design, they sit directly on top of the fingers and limit movement. U.S. Pat. No. 8,262,594 to Sandusky and Altenburger for a Reinforced Support Device includes stiffening components that slide into one big plate covering the back of the hand. This design does absorb some of the force but like U.S. Pat. No. 7,797,758 discussed above, one big plate covering the back of the hand is much more cumbersome than five individual plates which the present invention incorporates. Also, the design in U.S. Pat. No. 8,262,594 allows the back of the stiffening components to slide into the plate, allowing front to back movement for the fingers but since only one plate is used if more than one stiffening component slides into the plate at the same time side to side movement of the fingers will be limited as the backs of the stiffening components will come into contact with one another under the plate.

The present invention uses a strip made of elastic, or other stretchable material, to keep the stiffening component taut when the finger accompanying it is straightened. The prior art does include similar, but different, designs for using a strip of elastic, or other stretchable material. U.S. Pat. No. 7,406,720 to Hoelscher for a Glove With Support For Hyper-Extension Resistance includes "elastically stretchable strips" which are placed on both the palm and dorsal sides of the finger elements to enhance curl and assist with grip. The elastic, or other stretchable material, strip used in the present invention is only used on the stiffening components, does not touch the palm of the glove and does not assist with grip. U.S. Pat. No. 6,918,137 to Fowler for a Protective Hand Guard uses "bands" and "flexible linkages" to fasten "digit guards" to a glove. These bands and flexible linkages do provide freer movement of the fingers but do nothing to prevent the fingers from hyper-extending. Like the previously mentioned patents above, the Fowler digit guards sit directly on top of the fingers, limiting movement of the fingers. Also, the Fowler glove is designed to be used by health service providers to protect them from unwanted punctures from sharp implements such as hypodermic needles and does nothing to prevent hyper-extension. U.S. Pat. No. 8,678,980 to Land and Mantelmacher for a Low Profile Hand-Extension/Flexion Device includes a "spring member" which is attached directly to the finger portions of the glove to stretch joints for partially paralyzed victims and the elastic, or other stretchable material, strip of the present invention is attached to the top of stiffening components to pull it taut after the fingers have been bent. U.S. Pat. No. 8,029,414 to Ingvast et. al. for a Strengthening Glove includes "artificial tendons" attached to the inside of a glove but like U.S. Pat. No. 8,678,980 they are used to assist finger movement, in this case for strengthening the hand, and the present invention uses the elastic, or other stretchable material, strip to assist stiffening component movement. US 20050114982 A1 to Gremmert for a Reinforced Protective Glove includes "fastening strips" securing "phalangeal guards" while the present invention uses an elastic, or other stretchable material, strip to keep stiffening components taut. The phalangeal guards of US 20050114982 A1 are designed to protect the hand from blunt force trauma but do nothing to prevent hyper-extension. U.S. Pat. No. 8,849,453 to Bergelin et al. for a Human Grasp Assist Device includes a "flexible tendon" passing through a series of "phalange rings" that resembles a stiffening component but this flexible tendon is pulled by an actuator assembly to improve grasp strength for someone operating office equipment such as a keyboard while the elastic, or other stretchable material, strip used in the present invention is used to keep the stiffening component taut once the finger below it is moved forward.

BRIEF SUMMARY OF THE INVENTION

The present invention is a glove which prevents fingers from being hyper-extended or jammed by affixing stiffening components to the top of the distal, intermediate or proximal phalanges on the fingers and the top of the distal or proximal phalanx on the thumb with an anchoring component composed of a sliding swivel pivot hinge attached beyond each base knuckle; a slot in the sliding swivel pivot hinge allows it to be affixed to a protruding base which provides free movement of the finger enabling lateral, front to back, side to side as well as up and down movement while preventing the finger from hyper-extending.

BRIEF DESCRIPTION OF THE SEVERAL VIEWS OF THE DRAWING

Figures

DETAILED DESCRIPTION OF THE INVENTION

Figure 1:
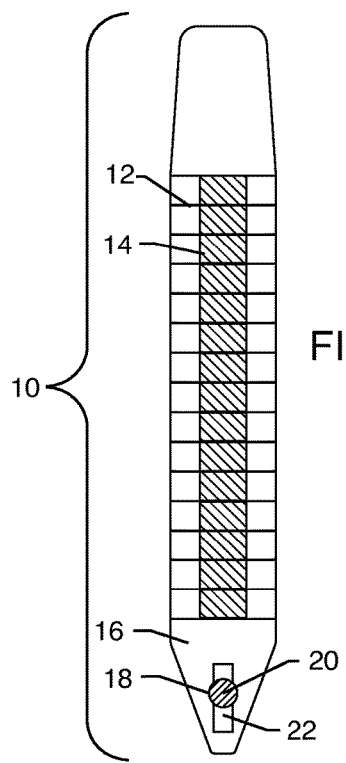
FIG. 1—Stiffening Component (top view)

FIG. 1 presents a perspective view of a stiffening component 10 (sized to the wearer's corresponding individual finger measurements) made of plastic or other sufficiently rigid and strong material. Slits 12 are shown in the middle of the stiffening component 10 and blocks 14 made of plastic or other sufficiently rigid and strong material are attached between each slit 12. This allows the stiffening component 10 to bend in conjunction with the wearer's finger and stiffen when the wearer's finger is straightened. A sliding swivel pivot hinge 16 including a protruding base 18 creates an anchoring component which locks at the wearer's base knuckle when the wearer's finger raises to approximately a 45 degree angle. This greatly reduces force and prevents the wearer's finger from hyper-extending or jamming. The top 20 of the protruding base 18 is slightly larger than a slot 22 cut into the sliding swivel pivot hinge 16 to allow the stiffening component 10 to move freely and prevent it from detaching.

Figure 2:
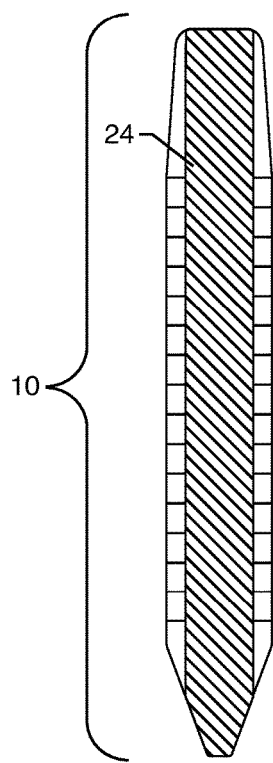
FIG. 2—Stiffening Component Covered with Optional Piece of Elastic or Other Stretchable Material (top view)

FIG. 2 presents a perspective view of stiffening component 10 with an optional strip of elastic 24 (or other stretchable material) attached at the front and back to allow bending but return the stiffening component 10 to a straight position when taut.

Figure 3:
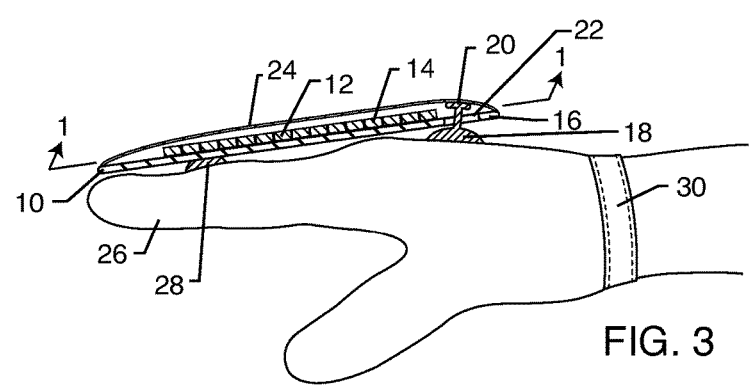
FIG. 3—Stiffening Component in Straight Position Attached to the Fore Finger Portion of a Non-Slip Glove (side view, right hand) with Anchoring Component Attached Beyond Base Knuckle FIG. 4—Stiffening Component in Curved Position Attached to the Fore Finger Portion of a Non-Slip Glove (side view, right hand) with Anchoring Component Attached Beyond Base Knuckle FIG. 5—Stiffening Components Attached to Each Finger and Thumb on a Non-Slip Glove (top view, left hand)

FIG. 3 presents a perspective view of stiffening component 10 in a straight position attached at the intermediate phalanx above the fore finger and just beyond base knuckle of a skin tight glove 26 covered in non-slip material (such as latex, rubber, silicone or comparable material). A pad 28 made of neoprene or other lightweight, flexible and durable material creates a cushion and allows the stiffening component to move freely. Optional piece of elastic 24 (or other stretchable material) is taut, closing the slits 12 and pressing all the blocks 14 together transforming the stiffening component 10 into a solid element which stops when it hits the protruding base 18 of sliding swivel pivot hinge 16 via the slot 22 and prevents finger from hyper-extending or jamming. The top 20 of protruding base 18 prevents the stiffening component 10 from detaching from glove 26. A wrist wrap 30 made of elastic (or other comparable material) and a hook and loop fastener is attached to the base of the glove 26 and wrapped around wearer's wrist to keep the glove 26 in place.

Figure 4:
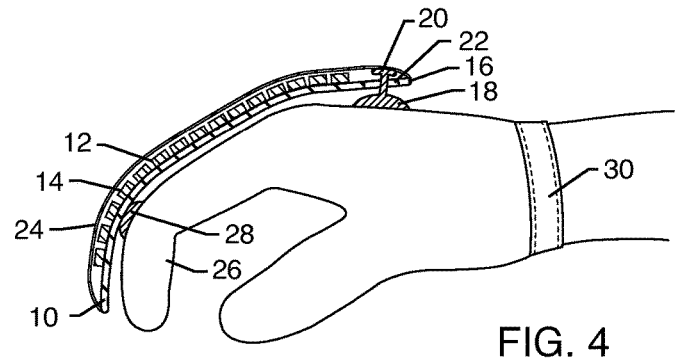

FIG. 4 presents a perspective view of the same stiffening component 10 attached at the intermediate phalanx above the fore finger and just beyond base knuckle of glove 26 in a curved position. A pad 28 made of neoprene or other lightweight, flexible and durable material creates a cushion and attaches the stiffening component 10 to the glove 26 while allowing the stiffening component 10 to move freely. When the wearer's finger is bent the optional piece of elastic 24 (or other stretchable material) stretches, opening the slits 12 and moving the blocks 14 in the same curved position as the finger. Slot 22 allows the stiffening component 10 to move forward while the protruding base 18 of sliding swivel pivot hinge 16 anchors the back of the stiffening component 10 to the glove 26. The top 20 of protruding base 18 prevents the stiffening component 10 from detaching from glove 26. A wrist wrap 30 made of elastic (or other comparable material) and a hook and loop fastener is attached to the base of the glove 26 and wrapped around wearer's wrist to keep the glove 26 in place.

Figure 5:
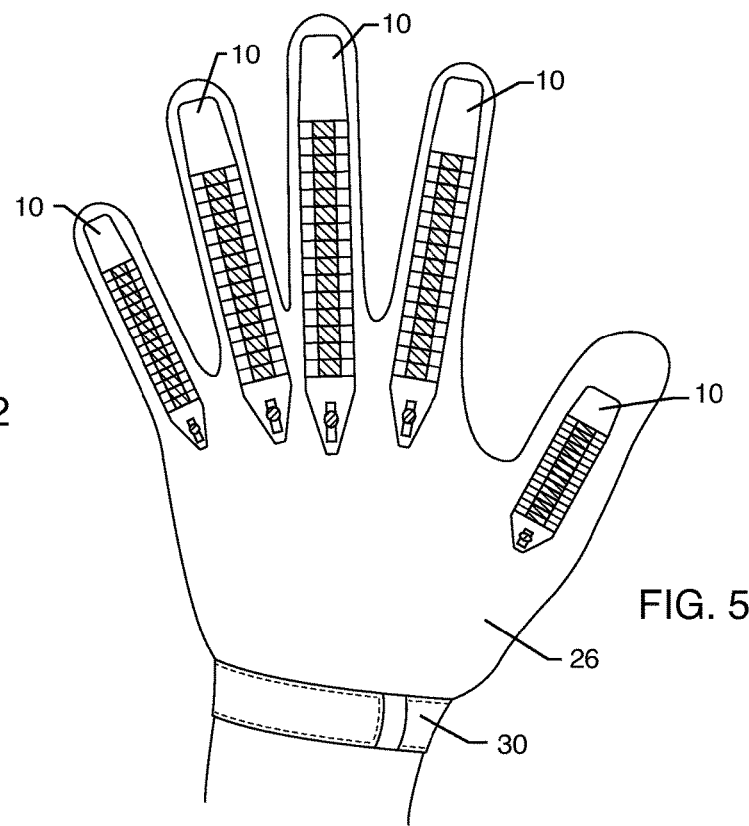

FIG. 5 presents a perspective view of the stiffening components 10 (sized to the wearer's corresponding individual finger and thumb measurements) attached to glove 26 for all fingers and thumb which curve when wearer's fingers are bent but stiffen when wearer's fingers are straightened. Stiffening components 10 are sized to the exact measurements of wearer's fingers and are attached to the top of the intermediate phalanges on the fingers and the top of the proximal phalanx on the thumb with an anchoring component attached beyond each base knuckle. A wrist wrap 30 made of elastic (or other comparable material) and a hook and loop fastener is attached to the base of the glove 26 and wrapped around wearer's wrist to keep the glove 26 in place.

Figure 6:
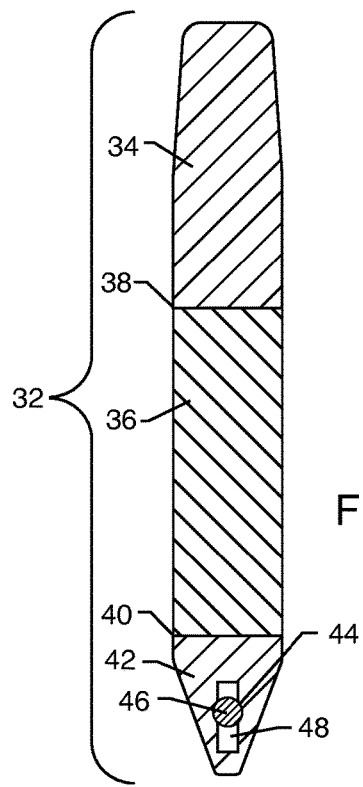
FIG. 6—Alternate Stiffening Component Made of Planks Rather than Blocks (top view)

FIG. 6 presents a perspective view of an alternate stiffening component 32 which is composed of an intermediate phalanx plank 34 (sized in correspondence to the wearer's individual finger measurements), a proximal phalanx plank 36 (sized in correspondence to the wearer's individual finger measurements) and a sliding swivel pivot hinge 42. The back of the intermediate phalanx plank 34 is connected to the front of the proximal phalanx plank 36 with a front hinge 38 and the back of the proximal phalanx plank 36 is connected to the front of the sliding swivel pivot hinge 42 with a back hinge 40. The alternate stiffening component 32 works in the same manner as the stiffening component 10 mentioned above with front hinge 38 and back hinge 40 serving the same purpose as slits 12 and blocks 14 allowing the stiffening component 32 to bend and straighten in conjunction with the wearer's finger. Like the sliding swivel pivot hinge 16 with protruding base 18 above, sliding swivel pivot hinge 42 with protruding base 44 create an anchoring component which locks at the wearer's base knuckle when the wearer's finger raises to approximately a 45 degree angle. This greatly reduces force and prevents the wearer's finger from hyper-extending or jamming. The top 46 of the protruding base 44 is slightly larger than a slot 48 cut into the sliding swivel pivot hinge 42 to allow the stiffening component 32 to move freely and prevent it from detaching.

Figure 7:
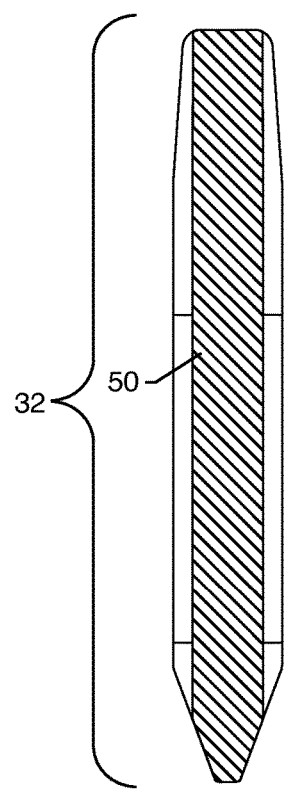
FIG. 7—Alternate Stiffening Component Covered with Optional Piece of Elastic or Other Stretchable Material (top view)

FIG. 7 presents a perspective view of alternate stiffening component 32 with an optional strip of elastic 50 (or other stretchable material) attached at the front and back to allow bending but return the stiffening component 32 to a straight position when taut.

Figure 8:
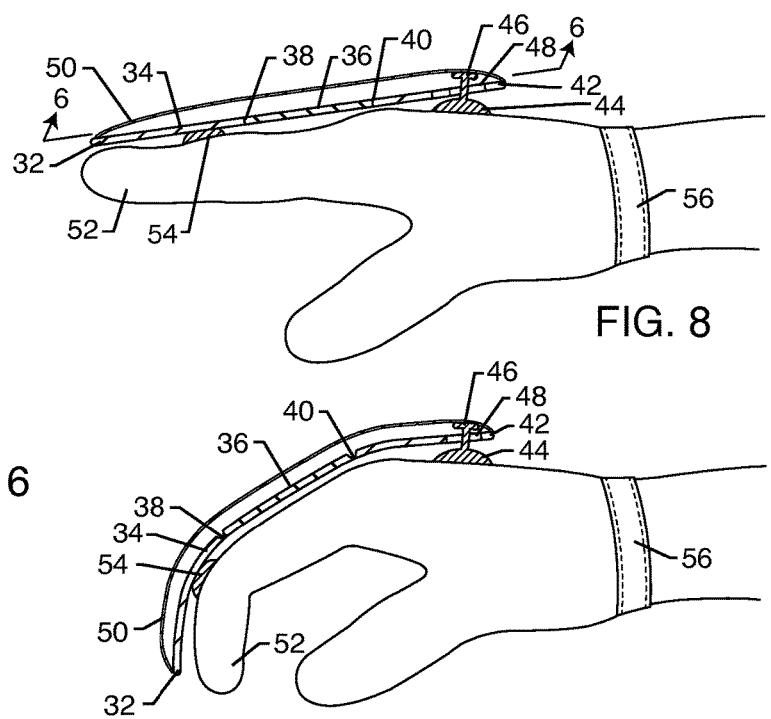
FIG. 8—Alternate Stiffening Component in Straight Position Attached to the Fore Finger Portion of a Non-Slip Glove (side view, right hand) with Anchoring Component Attached Beyond Base Knuckle FIG. 9—Alternate Stiffening Component in Curved Position Attached to the Fore Finger Portion of a Non-Slip Glove (side view, right hand) with Anchoring Component Attached Beyond Base Knuckle FIG. 10—Alternate Stiffening Components Attached to Each Finger and Thumb on a Non-Slip Glove (top view, left hand)

FIG. 8 presents a perspective view of alternate stiffening component 32 in a straight position attached at the intermediate phalanx above the fore finger and just beyond base knuckle of a skin tight glove 52 covered in non-slip material (such as latex, rubber, silicone or comparable material). A pad 54 made of neoprene or other lightweight, flexible and durable material creates a cushion and attaches the stiffening component 32 to the glove 52 while allowing the stiffening component 32 to move freely. Optional piece of elastic 50 (or other stretchable material) is taut, closing front hinge 38 and pressing the intermediate phalanx plank 34 against the proximal phalanx plank 36 and also closing back hinge 40 pressing the proximal phalanx plank 36 against sliding swivel pivot hinge 42 transforming the stiffening component 32 into a solid element which stops when it hits the protruding base 44 of sliding swivel pivot hinge 42 via the slot 48 and prevents finger from hyper-extending or jamming. The top 46 of protruding base 44 prevents the stiffening component 32 from detaching from glove 52. A wrist wrap 56 made of elastic (or other comparable material) and a hook and loop fastener is attached to the base of the glove 52 and wrapped around wearer's wrist to keep the glove 52 in place.

Figure 9:
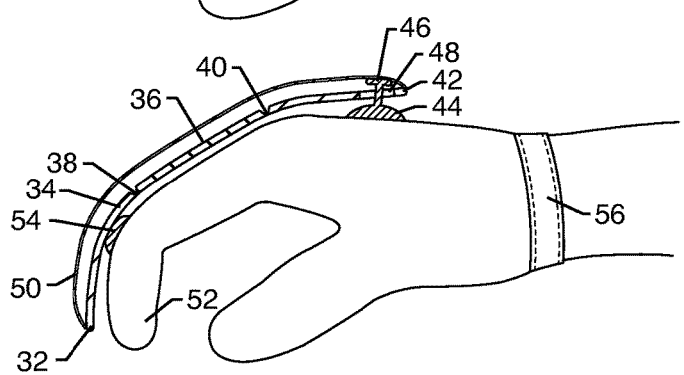

FIG. 9 presents a perspective view of the same alternate stiffening component 32 attached at the intermediate phalanx above the fore finger and just beyond base knuckle of glove 52 in a curved position. A pad 54 made of neoprene or other lightweight, flexible and durable material creates a cushion and allows the stiffening component to move freely. When the wearer's finger is bent the optional piece of elastic 50 (or other stretchable material) stretches, opening front hinge 38 and back hinge 40 and moving the intermediate phalanx plank 34 and proximal phalanx plank 36 in the same curved position as the finger. Slot 48 allows the stiffening component 32 to move forward while the protruding base 44 of sliding swivel pivot hinge 42 anchors the back of the stiffening component 32 to the glove 52. The top 46 of protruding base 44 prevents the stiffening component 32 from detaching from glove 52. A wrist wrap 56 made of elastic (or other comparable material) and a hook and loop fastener is attached to the base of the glove 52 and wrapped around wearer's wrist to keep the glove 52 in place.

Figure 10:
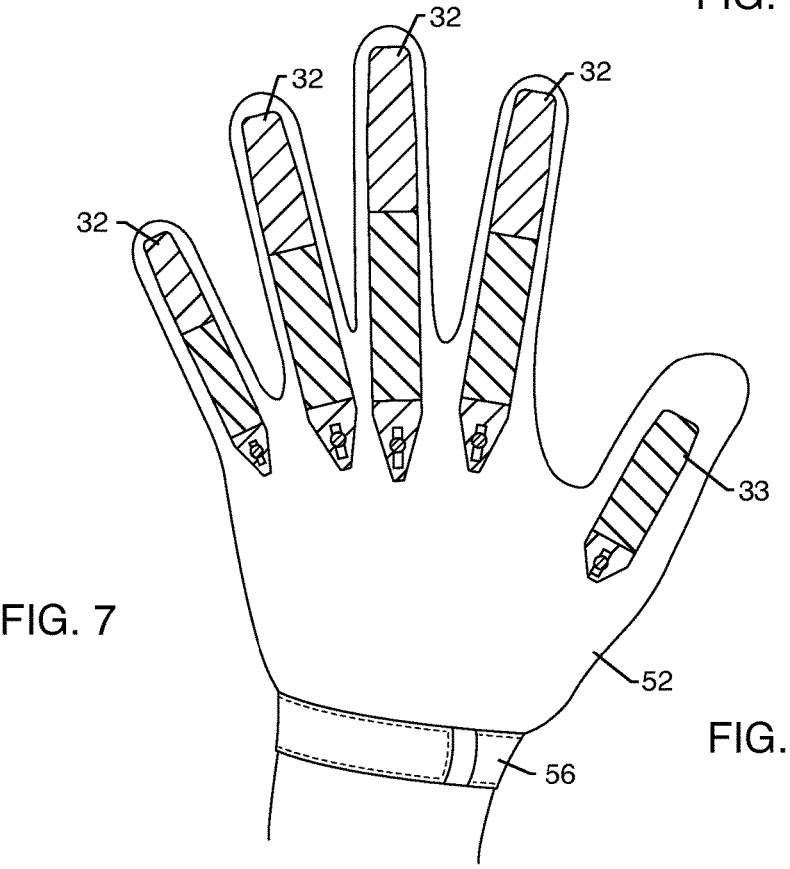

FIG. 10 presents a perspective view of the alternate stiffening components 32 (sized to the wearer's corresponding individual finger and thumb measurements) attached to glove 52 for all fingers and thumb which curve when wearer's fingers are bent but stiffen when wearer's fingers are straightened. Stiffening components 32 are sized to the exact measurements of wearer's fingers and are attached to the top of the intermediate phalanges on the fingers and the top of the proximal phalanx on the thumb with an anchoring component attached beyond each base knuckle. The alternate stiffening component for thumb 33 does not have the intermediate phalanx plank as thumbs do not have intermediate phalanges. A wrist wrap 56 made of elastic (or other comparable material) and a hook and loop fastener is attached to the base of the glove 52 and wrapped around wearer's wrist to keep the glove 52 in place.

FIGS. 3, 4, 8 and 9 present perspective views of a single stiffening component attached to the glove. This design is for sports such as basketball or volleyball where one finger, in this case the fore finger, has been injured and the stiffening component assists in preventing further injury. In scenarios where only one stiffening component is needed, the stiffening component can be attached directly to the front of the injured finger, using tape or other means, and the anchoring component of the sliding swivel pivot hinge can be attached to a fingerless glove (not shown).

FIGS. 5 and 10 present perspective views of multiple stiffening components attached to the glove. This design is for sports such as football, soccer, snowboarding or motorcycle riding and work such as construction or heavy machinery operation where all four fingers and the thumb need to be protected.

Not Pictured. Two elements of the invention which are not shown in the drawings is a dorsal side cover that will cover the back of the glove including all stiffening components. Also, a second alternate stiffening component, where the elements comprising the stiffening component are made of "Z" shaped blocks rather than the rectangular shaped blocks which are shown in the original stiffening component shown in FIGS. 1 through 5.

I claim:

1. A glove for protecting a wearer's fingers and thumb from hyper-extension or jamming, comprising:
    a palm side layer having a palm portion with four finger portions and a thumb portion extending therefrom configured to cover the palm side of a wearer's hand including the wearer's fingers and thumb;
    a first hand shaped dorsal side layer configured to cover a back of a wearer's hand including over said wearer's four fingers and thumb:
    a second hand shaped dorsal side layer configured to cover the back of the wearer's hand over a series of finger stiffening components;
    a wrist covering portion;
    said palm side layer and said first and second hand shaped dorsal side layers are joined about said palm portions, said wrist covering portion, said four finger portions and said thumb portion to create a receptacle area for the wearer's palm, wrist, four fingers and thumb between said palm side layer and said first hand shaped dorsal side layer; and to create a finger stiffening component receptacle area between said first hand shaped dorsal side layer and said second hand shaped dorsal side layer;
    and finger stiffening components configured for each finger of said four fingers and said thumb and placed within each said four finger and thumb stiffening component receptacle areas;
    said finger stiffening components are each comprised of a series of blocks placed end to end followed by a sliding swivel pivot hinge, each swivel hinge affixed to a strip of material; said sliding swivel pivot hinge including a housing unit having a slot and a protruding base that has a bottom, a rod and a top; said top of the protruding base being wider than the slot and affixed to a top of the rod to thereby prevent said stiffening component from detaching from said glove when attached to said glove.

2. A glove for protecting a wearers fingers and thumb from hyper-extension or jamming as claimed in claim 1, and further comprising:
    wherein each finger stiffening component is comprised of an intermediate phalanx plank placed next to a proximal phalanx plank placed next to a sliding swivel pivot hinge with each affixed to a strip of material.

3. A glove for protecting a wearer's fingers and thumb from hyper-extension or jamming as claimed in claim 1, and further comprising:
    wherein said strip of material is made of an elastic or felt flexible material.

4. A glove for protecting a wearer's fingers and thumb from hyper-extension or jamming as claimed in claim 1, and further comprising:
    wherein the blocks are affixed, end to end on said strip of material by glue.

5. A glove for protecting a wearer's fingers and thumb from hyper-extension or jamming as claimed in claim 1, and further comprising:
    the sliding swivel pivot hinge placed at one end of the blocks and the bottom of each block and the bottom of the sliding swivel pivot hinge and that is affixed to the strip of material by glue.

6. A glove for protecting a wearer's fingers and thumb from hyper-extension or jamming as claimed in claim 1, and further comprising:
    the blocks as being made of plastic and are in a rectangular shape or in a "Z" shape with a top that extends slightly outward to in a left direction and a bottom extends slightly in a rightward direction.

7. A glove for protecting a wearer's fingers and thumb from hyperextension or jamming as claimed in claim 4, and further comprising:

the finger stiffening components include the series of blocks affixed to the material strip with spaces located between each block to thereby allow bending between the stiffening component when curved but form a line of blocks that are adjacent to each other without spaces therebetween when in a straight line as the blocks press against each other when straightened.

8. A glove for protecting a wearer's fingers and thumb from hyper-extension or jamming as claimed in claim 1, and wherein:

said housing unit and protruding base are made of plastic.

9. A glove for protecting a wearer's fingers and thumb from hyper-extension or jamming as claimed in claim 1, and wherein:

said protruding base bottom is affixed to a back of the first dorsal side of the glove by glue.

10. A glove for protecting a wearer's fingers and thumb from hyper-extension or jamming as claimed in claim 1, and wherein:

the rod of the protruding base passes through the slot in the housing unit-.

11. A glove for protecting a wearer's fingers and thumb from hyper-extension or jamming as claimed in claim 1, and wherein:

a top of the protruding base, which is wider than the slot, is affixed to the top of the rod thereby preventing the stiffening component from moving past a 45 degree angle and preventing a hyper-extended or jammed finger when the rod hits the front of the slot.

\* \* \* \* \*